United States Patent
Takeshita et al.

(10) Patent No.: US 6,593,129 B1
(45) Date of Patent: Jul. 15, 2003

(54) APPARATUS FOR MICROINJECTION OF SAMPLE INTO AMPHIBIAN OOCYTES

(75) Inventors: Tomoko Takeshita, Higashimatsuyama (JP); Jun Otomo, Tokyo (JP); Sayuri Nomura, Higashimatsuyama (JP); Shokichi Matsunami, Tokorozawa (JP); Noboru Moriya, Tokorozawa (JP); Sakae Saito, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 102 days.

(21) Appl. No.: 09/666,530

(22) Filed: Sep. 20, 2000

(30) Foreign Application Priority Data

Aug. 25, 2000 (JP) ........................................ 2000-256381

(51) Int. Cl.[7] .............................................. C12M 1/00
(52) U.S. Cl. ................................ 435/285.1; 435/172.2; 435/286.2; 435/286.4; 435/288.7
(58) Field of Search .......................... 435/285.1, 286.2, 435/286.4, 288.7, 172.1, 172.2; 600/345

(56) References Cited

U.S. PATENT DOCUMENTS

| | | | |
|---|---|---|---|
| 4,593,646 A | | 6/1986 | Miller et al. |
| 4,907,158 A | * | 3/1990 | Kettler et al. ............... 382/128 |
| 5,114,854 A | * | 5/1992 | Bertholdt ................. 435/285.1 |
| 5,183,744 A | | 2/1993 | Kawamura et al. ........... 435/30 |
| 5,516,490 A | | 5/1996 | Sanadi ....................... 422/101 |
| 6,470,201 B2 | * | 10/2002 | Kato et al. .................. 600/345 |

FOREIGN PATENT DOCUMENTS

| | | | |
|---|---|---|---|
| DE | 40 04 198 A1 | 2/1990 | |
| DE | 19721084 A1 | * 11/1998 | ............ C12M/1/26 |
| JP | 63-101098 | 12/1986 | |
| JP | 64-3560 | 5/1988 | |
| JP | 1-112976 | 5/1989 | ............ C12M/1/00 |
| JP | 3-259076 | 3/1990 | |
| JP | 5-192171 | 8/1993 | |
| JP | 6-343478 | 12/1994 | |
| WO | WO 83/00047 | 6/1982 | |

OTHER PUBLICATIONS

European Search report dated Aug. 13, 2002.

* cited by examiner

Primary Examiner—David A. Redding

(57) ABSTRACT

An apparatus for microinjection of samples into amphibian oocytes, comprising a tray for holding a plurality of the amphibian oocytes, an injection needle for injecting a sample into the said amphibian oocytes, a driving means for moving a relative position between the said tray and the said injection needle and a controlling means for controlling the said movement by imputing a depth of the said injection needle for the said tray or the said amphibian oocytes in the injection of the sample, and injecting the sample into the said amphibian oocytes at the said depth.

According to the present invention, the sample can be injected into the amphibian oocyte with constant depth.precisely and quality of oocyte or a positional site of needle injection can be recorded as the information.

27 Claims, 6 Drawing Sheets

|        | the number of oocytes | the number of responding oocytes |
|--------|-----------------------|----------------------------------|
| light  | 40                    | 34                               |
| dark   | 28                    | 1                                | gene injection 24 hour culture sample containing histamine sample without histamine

APPARATUS FOR MICROINJECTION OF SAMPLE INTO AMPHIBIAN OOCYTES

BACKGROUND OF THE INVENTION (1) Technical Field

The present invention relates to an automated apparatus for injecting a sample of gene, pigment, protein, peptide or drug into oocytes of Amphibia such as frog using a pipette-like needle. The present invention further pertains a method for injecting the sample of gene, pigment, protein, peptide or drug into the specified position of the amphibian oocytes, the amphibian oocytes with a guaranteed quality for injection of the sample, and a method for selling or assigning the amphibian oocytes into which the sample is injected at a specified position and depth.

(2) Background Art

Since oocytes of frogs such as Xenopus lavis, into which gene, pigment, protein, peptide or drug is injected, have a comparatively large size and can be obtained with a low cost and in large quantities, they are widely used for the purpose of confirming actions of pigment, protein, peptide and drug on viable cells, analysis of gene functions, and production of proteins as a gene product. To this purpose, the individual research scientists breed frogs by themselves and collect the oocytes.

Heretofore, in the injection of a sample such as gene, pigment, protein, peptide and drug into the oocytes of Amphibia such as frog, technicians manually injected with a pipette-like needle in which these samples are packed, into the oocytes under a microscopic observation using a manipulator. The pipette is mounted on the injector and a constant amount of sample is injected and exhaled into cells by an action of an oil pressure or an air pressure. Further, JP-A-5-192171 and JP-A-6-343478 disclose a method for injection and exhalation of a constant amount of sample into cells by applying a voltage. These prior arts disclose techniques for injection of sample by approaching needle manually to the cell under observing the cell microscopically.

SUMMARY OF THE INVENTION (1) Problems to be Solved by the Invention

The above manual injection of samples such as genes had a problem that a rate of oocytes, into which sample was successfully injected, was varied depending on skills and experiences of technicians. This was due to a difference in numbers of oocytes, into which the sample could be injected within a fixed time, depending on the individual technician, and as a result, a degree of denaturation of the sample was varied in a time-dependent manner among the technicians. It is an object of the present invention to provide a method to give a constant numbers of cells per hour to be treated independent of the skills and experiences of the technicians.

Further, the above described prior art did not take into the for unifying of the injection depth of samples into the oocytes at a constant depth. Consequently, it was difficult to control the depth even by a skilled technician. As a result, an injection of a sample into a specified cell organelle such as a nucleus had to depend on chance. It is another object of the present invention to provide an easier method for injecting a sample into a cellular organelle such as a nucleus, in which the injection can be controlled in a depth direction by unifying the injection depth of the sample.

Furthermore, in the above described prior art, since no consideration was given for memorizing information of cells in the injection of the sample, it was difficult to obtain a correlation between the information on the sample injection and the subsequent cell reaction. Consequently, it is further object of the present invention to provide a method for obtaining the correlation between them.

In addition, in the conventional techniques, the oocytes were prepared individually and thus a mass production or production on demand in good time was impossible.

Consequently, it is a further object of the present invention to provide the oocytes, into which a specified sample is injected, or the production, sale and transportation of the oocytes with a guaranteed injection of the specified sample at a constant position.

(2) Means for Solving the Problems

In order to solve the above problems, the present invention provides an apparatus for automatically injecting the sample such as gene, pigment, protein, peptide or drug into any constant position and any constant depth of the oocytes of Amphibia such as frogs by using a pipette-like needle.

Namely, the present invention provides an apparatus for microinjection of samples into amphibian oocytes comprising a tray for holding a plurality of the amphibian oocytes, an injection needle for injecting a sample into the said amphibian oocytes, a driving means for moving a relative position of the said tray to the said injection needle and a controlling means for controlling the said movement by inputting a depth of the said injection needle for the said tray or the said amphibian oocytes in the injection of the sample, and injecting the sample into the said amphibian oocytes at the said depth.

The present invention further provides a system for microinjection of samples into amphibian oocytes comprising a tray for holding a plurality of the amphibian oocytes, an injection needle for injecting sample into the said amphibian oocytes, a driving means for moving a relative position of the said tray to the said injection needle in a three dimensional direction, a controlling means for controlling the said movement, an information obtaining means for obtaining visual information on the said amphibian oocytes in the microinjection, and a memorizing means for accumulating the said information, and injecting the said sample into the said amphibian oocytes.

As a result, the sample can be injected rapidly into the plurality of amphibian oocytes at an almost constant depth.

Further, the tray has a plurality of wells having a cylindrical structure with a flat base or with a conical base having a maximum diameter of 105–150% of a diameter of the amphibian oocytes. As a result, the sample can be injected into the identical surface in about 80% of oocytes on the tray without applying any special means.

We have found that when mRNA was injected into the oocytes, in case that mRNA was injected into the animal hemisphere of the oocyte or mRNA was injected into the vegetal hemisphere, expression efficiency or the functional expression efficiency is different. Namely, in order to suppress a variation of the expression efficiency of the function of a protein in oocytes, it is important to collect the oocytes, in which mRNA is injected into the same hemispherical surface. In the present invention, it is possible to memorize information of cellular area in the injection of the sample and to induce easily a correlation between the information and the subsequent cell reaction.

Further, the present invention provides a method for automatic microinjection of samples into amphibian oocytes comprising,
  using an apparatus having a tray for holding a plurality of the amphibian oocytes and an injection needle for injecting a sample into a plurality of the said amphibian oocytes, a step for setting a depth of the said injection needle for the said tray or the said amphibian oocytes at the first depth, a step for injecting the sample into the first oocyte in a plurality of the said amphibian oocytes using the said injection needle at the said first depth, a step for automatically moving a relative position of the said tray to the said injection needle, and a step for subsequently injecting the sample into the second oocyte in a plurality of the said amphibian oocytes by using the said injection needle to the said first depth.

Furthermore, the present invention provides a method for automatic microinjection of samples into amphibian oocytes comprising, using an apparatus having a tray for holding a plurality of the amphibian oocytes and an injection needle for injecting a sample into a plurality of the said amphibian oocytes, a step for injecting the sample into the first oocyte in a plurality of the said amphibian oocytes using the said injection needle, a step for moving a relative position of the said tray to the said injection needle, a step for subsequently injecting the sample into the second oocyte in a plurality of the said amphibian oocytes using the said injection needle, a step for obtaining a condition of oocyte in the injection of the said sample as a visual information, and a step for accumulating the said visual information.

According to the invention of the above described apparatus or method for injection of the sample into the amphibian oocytes, the present invention further provides a plurality of the amphibian oocytes wherein the sample is injected under a substantially equal condition in the injection depth of the sample.

The present invention also provides the said amphibian oocytes wherein the sample is further injected under a substantially same condition in the injection position of the sample.

In addition, the present invention provides the following methods.

A method for preparation of a group of the amphibian oocytes injected with a sample comprising, using an apparatus having a tray for holding a plurality of the amphibian oocytes and an injection needle for injecting sample into a plurality of the said amphibian oocytes, moving a relative position of the said injection needle to the said tray, injecting the sample into each of a plurality of the said respective amphibian oocytes using the said injection needle, obtaining each visual information of the said amphibian oocytes in the injection, and collecting a plurality of the oocytes in which the sample is injected into the animal hemisphere of the oocyte, or a plurality of the oocytes in which the sample is injected into the vegetal hemisphere of the oocyte in a plurality of the said amphibian oocytes based on the said visual information.

A method for selling or assigning a plurality of the amphibian oocytes comprising selling or assigning as a set a plurality of the amphibian oocytes, into which the sample is injected under a substantially equal condition in the injection depth of the sample, and attaching the information on the injection of the sample into a plurality of the amphibian oocytes to the set.

In addition, a method for selling or assigning a plurality of the amphibian oocytes comprising putting a plurality of the amphibian oocytes into which the sample is injected under a substantially equal condition in the injection depth of the sample into a vessel, and attaching a label on which the information on the injection of the sample into a plurality of the said amphibian oocytes is described to the said vessel.

In this connection, the information on the injection of the sample into a plurality of the amphibian oocytes relates to at least any one of a date and time of the injection, a term for guarantee of a quality, a position where the sample is injected, a depth at which the sample is injected and a probability of expression.

As a result, according to the present invention, the oocytes having substantially identical condition in relation to the injections as well as their information can be obtained.

EXPLANATION OF SYMBOLS

Figure 1:
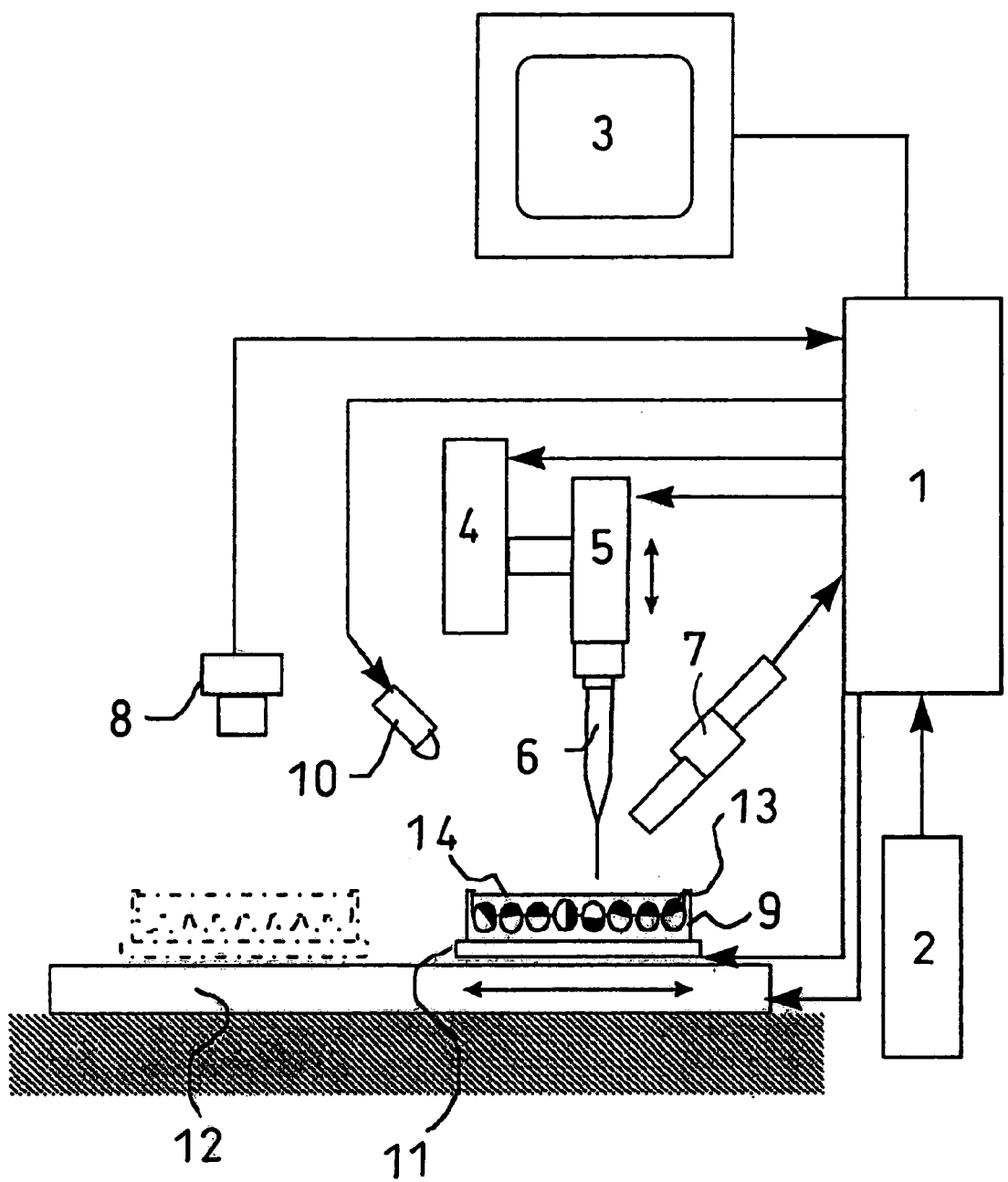
FIG. 1. A construction of apparatus of the present invention.

1: control unit, 2: auxiliary control unit, 3: monitor, 4: moving table for injection needle, 5: injection device, 6: injection needle, 7: CCD camera, 8: digital camera, 9: tray, 10: light source, 11: orthogonal moving table, 12: horizontal moving table, 13: oocytes, 14: physiological saline for Amphibia, 21: vessel, 22: label, 23: cold insulator, 31: histamine receptor gene, 32: histamine receptor, 33: sample containing histamine, 34: histamine response (positive), 35: sample without histamine, 36: histamine response (negative), 41: syringe, 42: buffer solution for Amphibia, 43: antibiotics, 44: outer vessel, 45: package.

DESCRIPTION OF THE PREFERRED EMBODIMENT

Referring to the drawings, the present invention will be explained in detail in the following.

In FIG. 1, the principle of the present apparatus is shown.

Figure 2:
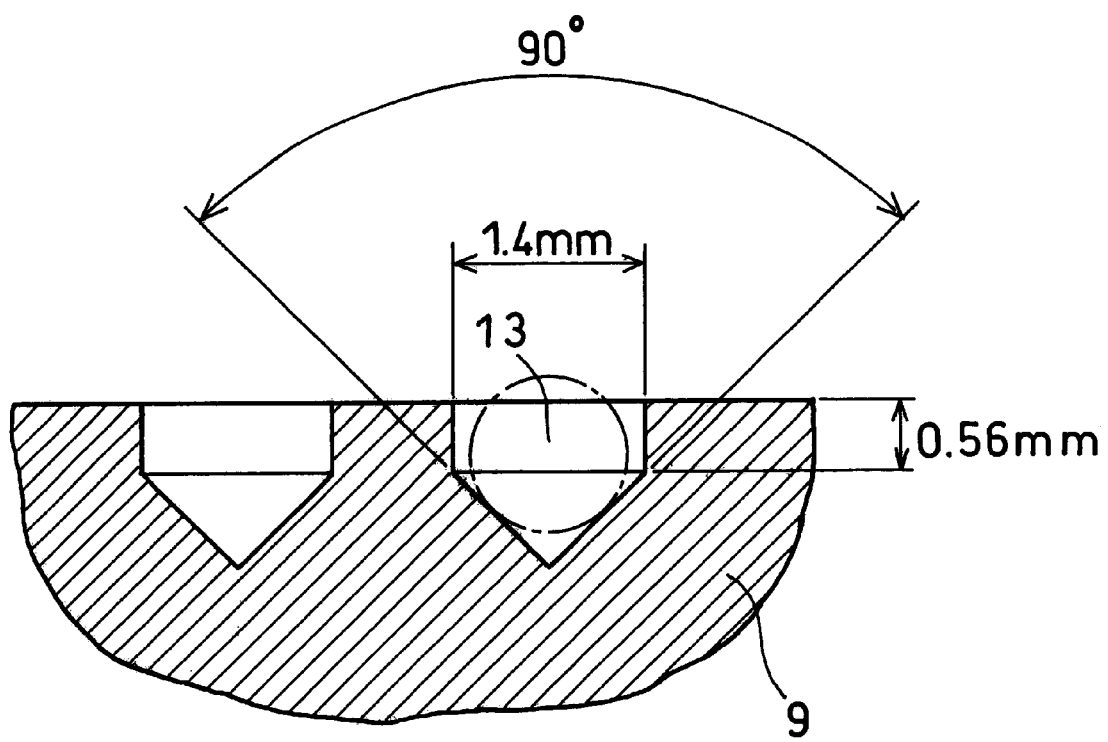
FIG. 2. An illustrative example of a tray used in the present invention.

A tray, in which the oocytes are lined up and arranged, having, for example, arrangements of 12 wells in a horizontal direction and 8 wells in an orthogonal direction, in total 96 wells with an uniform depth and form, can be used, however the number of wells are not limited to 96 wells. The amphibian oocytes have generally a heavier weight in the vegetal hemisphere than in the animal hemisphere. Consequently, by designing a diameter of the well in the tray to be slightly larger than that of the oocytes in use, about 80% of the oocytes in average can be maintained to keep their animal hemispheres upside, without changing the directions of oocytes arranged on the tray by rotating the cells, and the injection probability to the identical hemispherical surface can be increased up without using any other special means. A form of a well for arranging oocytes is preferably a cylindrical form, which has a circular flat basal plane with a constant cross section parallel to the base plane from the base plane to the open end aperture of the above well, or a form with a conical base. A diameter of the open end of the above well should be larger than that of the amphibian oocytes in use. In addition, due to the above-mentioned reason, it is preferable to keep a space for rotating the oocytes in a well in which physiological saline is filled, and specifically the fact that a maximum diameter of the well set as 105–150% of the diameter of oocytes in use is preferable, has been confirmed experimentally. For example, since the diameter of Xenopus oocytes is approximately 1.3 mm, it becomes possible to fix the oocytes in a specified direction without damaging the oocytes by designing the diameter of a well as about 1.4–2 mm. Preferable form of a well in the present invention is, for example, as shown in FIG. 2, a conical shaped well with an angle of base at 90°, diameter 1.4 mm and depth in cylindrical part 0.56 mm. Furthermore, by using a syringe in addition to the use of the above tray, it is possible to operate with an increased injection probability into the same surface sides of different oocytes or it is possible to operate so that the specified surface, for example, the vegetal hemispheres of the oocytes are directed upward.

Examples of samples to be injected include, but are not limited to gene, pigment, protein, peptide, and drugs. In the example herein below, oocytes, into which histamine receptor cRNA is injected, will be described, but an injectable gene is not limited to cRNA and can be DNA, RNA and synthetic oligonucleotides. A needle for injecting a sample is preferably a pipette-like needle, but is not limited .thereto. In order to obtain the cell information such as the positional direction of oocytes, visual information through the digital camera 8 is applied. Further, a means for detecting the contact of the injection needle 6 with the surface of oocyte is exemplified as the visual information through CCD camera 7. However, a means required for obtaining the information is not limited to the digital camera 8 and CCD camera 7. For example, a sensor, which can detect changes in pressure, temperature, voltage, moisture or pH, may be mounted on the injection apparatus, and the surface of oocytes can be detected based on these types of information.

The oocytes before injection of the sample are arranged in the wells on the tray 9, the physiological saline 14 is filled in the tray 9, and then the tray is set on the orthogonal moving table 11 and the horizontal moving table 12. It is preferable to determine the position of oocyte 13, to which the sample is injected from the injection needle 6, by controlling movement of the orthogonal moving table 11 and the horizontal moving table 12 to the direction for X-axis and the direction for Y-axis with the control unit 1. Contrary to the constitution in FIG. 1, however, the constitution can be applied by fixing the tray 9 with a movable injection needle 6.

When the tray 9 is located at the position of the broken line, the oocyte may be photographed by the digital camera 8, and to transfer the image data to the control unit 1, and the information of quality and positional direction of oocytes can be accumulated.

The horizontal moving table 12 and the orthogonal moving table 11 are operated by an indication of the control unit 1, and the center of the first oocyte 13, which is located in the defined position in the oocytes arranged on the tray 9, moves to the downward position under the position of the gene injection needle 6. At this point, the injection needle moving table 4 is operated by an indication of the control unit 1 for moving the injection needle to the direction of Z-axis, a tip of the injection needle 6 mounted on the injection unit 5 moves downward to the position slightly distant from the surface of the oocyte, for example, close to the front by several hundred mm. At this point, by observing the image taken by CCD camera 7 in the monitor 3, indication is given from the auxiliary control unit 2, and the injection needle moving table 4 , operated to descending direction slowly. The contact of the tip of the injection needle 6 with the surface of the oocyte 13 can be detected by visual information, pressure changes, temperature changes, electric changes, moisture changes, or pH changes, then the injection needle moving table 4 is stopped at this position. This position is a reference point for the subsequent gene injection operation. This point is made to be memorized in the control unit 1 and the following operation is performed. Namely, moving distance and depth of the injection needle for the vertical direction against a plane of the tray from the above reference point to the position of injecting sample are set, and the injection needle 6 is stuck at the setting depth to inject the previously fixed amount of the sample. For the injection of the sample, a control for Z-axis direction can be performed, for example, the injection needle moves downwardly to 0.2 mm from the contact point of the injection needle 6 on the surface of oocyte 13. The optimum injection depth of the injection needle 6 into the oocyte is different depending on the type of sample to be injected and the object for injection and can be set freely. The sample can not diffuse into the oocyte, if the injection depth is too shallow, and if it is too deep, the probability for damaging a nucleus and a oocyte is increased. Consequently, it is preferable to inject a sample at the almost constant depth from the standpoint of expression efficiency. For example, in the case that mRNA is injected into the cytoplasm in order to express a protein, sticking the needle to the depth of 0.02–0.1 mm from the cell surface is preferable. On the other hand, in the case that DNA is injected into a nucleus in order to express a protein, sticking the needle to the depth of 0.05–0.2 mm from the cell surface is preferable on the animal hemisphere. However, since the form of oocyte may be deformed at the injection, actually the sample is injected at the shallower position than the predetermined depth. Time for injecting the sample is controlled by setting time for inserting the needle in the oocyte depending on the amount of sample to be injected. In order to improve injection efficiency, a plurality of the injection needle 6 can be used. In this case, the movement of the relative position between the injection needle and the tray by the indication from the driving unit of the apparatus in one-dimensional direction or two-dimensional direction may be sufficient.

Subsequently, the sample is automatically injected at the indicated time, rate and injection depth into the desired numbers of other oocytes in the tray 9 by automatic control. Further, since size of oocytes may have some deviation, a function for detecting a position of the surface in each time of injection can be applied. In addition, the information of oocyte condition is memorized in the computer and is able to output on demand.

The system can be made so that the movement of the injection needle 6 and the oocyte 13 in the injection or the visual information of oocyte at the injection is memorized in the computer and after termination of injection operation, position and depth of sample injection, and characteristics of oocytes can be read out. In this case, the visual information of each oocyte is preferably related with its position on the tray by numbering the oocytes, for example.

The amphibian oocytes are known to exist for the animal hemisphere and the vegetal hemisphere, and each hemisphere has a different function. We have found that in cases that mRNA was injected into the oocyte, functional expression efficiency of protein was different in each case of injecting mRNA into the animal hemisphere and the vegetal hemisphere. In cases of injecting histamine receptor mRNA, the expression efficiency is higher in the injection into the animal hemisphere than the vegetal hemisphere; as a result, the oocyte with a large ligand response can be obtained. On the other hand, in cases that protein with fluorescent protein, or gene there of and pigment are injected, information on color and light with higher sensitivity can be obtained by the injection into the vegetal hemisphere. As described above, injection of sample into the animal hemisphere can be made for about 80% of oocytes on the tray by using the above tray. In cases that the oocytes, to which sample is injected into the specific surface of oocytes such as only for the animal hemisphere or the vegetal hemisphere, are expected to be obtained, as described above, each oocyte is treated for arranging the upward direction of the specific hemisphere by using a syringe before injection of sample. Alternatively, the area information for sample injection on the surface of oocytes is obtained by the detection means for visual information or by the black and white discrimination sensor in the injection of the sample, and as a result of the thus obtained information, the oocyte, to which the sample is injected into only the surface of interest directed for upward direction, can be collected. As a result, the oocytes having substantially identical conditions in the injected position can be obtained. In the present invention, the "specific area" means the position including the animal hemisphere, the vegetal hemisphere or the equatorial area of the oocytes.

By using of the apparatus having the above constitution, the sample can be injected into the specific area and depth of the amphibian oocytes, and the oocytes which have almost the same quality of the expression efficiency of the injected sample (injection efficiency), can be produced rapidly in mass production. Accordingly, the present invention provides a method for injecting a sample to the specific position and depth of the amphibian oocytes by using the apparatus of the present invention.

It is found that the sample injection efficiency can be improved by using the apparatus of the present invention as follows: Namely, in the case of beginners, who have no experience for sample injection by manual operation, about 30 minutes are required for injecting samples into 25 cells, and the injection efficiency is about 30% in case of the expression rate using a sample of gene. On the contrary, using the apparatus of the present invention, time for injecting samples into 25 cells requires only 3 minutes, and the injection efficiency reaches about 80%. In case of the sample injection performed by the experts with manual operation., almost no shortage of time for injection is observed, but the injection efficiency can be improved up to 90% by using the apparatus of the present invention as compared with efficiency of 80% in the manual operation.

Consequently, as a result of using the apparatus and method of the present invention, about 80–90% efficiencies can be achieved without depending upon the skill of the operators, and to sell or assign the plurality of oocytes with controlled condition of sample injection can be possibly achieved by the present invention.

Therefore, in the other aspect, the present invention provides the amphibian oocytes with guaranteed injection of the sample into the specific position and depth.

Figure 3:
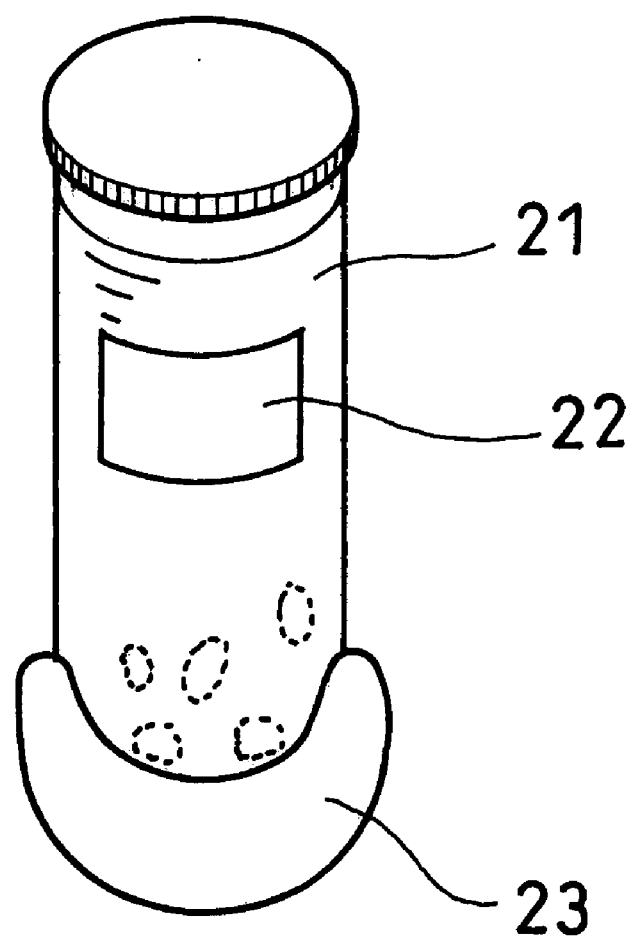
FIG. 3. An illustrative example of a vessel used in the present invention.

Further, the oocytes, to which the sample is injected in the specific area and depth, can be collected, sold or assigned. In the occasion of sale or assignment, a plurality of oocytes are packaged, and a label 22, in which the information on the the type of sample, the injection date, the term for guarantee of quality, setting condition such as the position and the depth of sample injection, and guaranteed injection efficiency are described, can be attached (FIG. 3).

According to the present invention, the oocytes can be sold or assigned with the information on the specific depth and area of the injection, and on the expression of protein encoded by the injected gene. In the event of selling or assigning the guaranteed oocytes regarding efficiency of sample injection or efficiency of expression, the efficiency of sample injection can be guaranteed, for example, by co-injecting a sample with protein containing pigment or chromophore, fluorescent protein, or gene encoding these proteins, counting numbers of oocytes emitting color or fluorescence, and indicating the ratio as an indicator of efficiency of sample injection. Although the coinjection can be performed in the mixed form, in cases that both the sample to be coinjected and protein for detection are injected in the form of gene, a gene coding fused protein can be used.

Figures 4, 5:
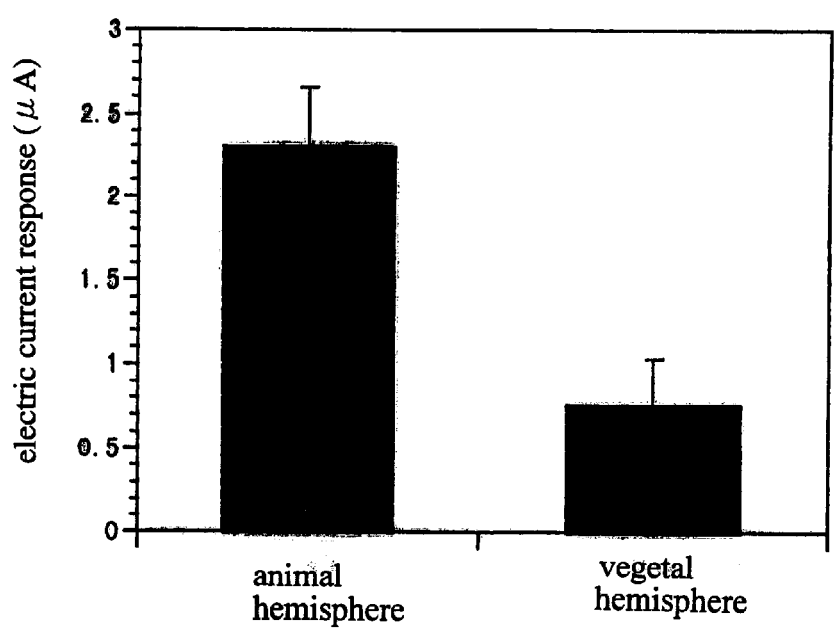
FIG. 4. A correlation between fluorescence of GFP injected into oocyte and a ligand response of histamine receptor expressed by co-injection.
FIG. 5. A correlation between an area of gene injection (animal hemisphere and vegetal hemisphere) and a ligand response.

Referring to FIG. 4, an example for calculating the efficiency of sample injection or efficiency of expression by using fluorescence from co-injected fluorescent protein as an indicator, will be explained. In the present example, when that rate of injection of histamine receptor gene is determined by using expression of the green fluorescent protein derived from Aequorea forbesiana (GFP) as an indicator, is explained. However, the injected samples are not limited to genes. Further, substances used for indicator of efficiency of sample injection are not limited to GFP.

A mixture of histamine receptor gene and green fluorescent protein gene is injected into the oocyte by using the apparatus assembled with the above constitution or the above principles. After 24 hours from gene injection manipulation, light of wavelength at 488 nm is irradiated on the oocytes, and then the expressed green fluorescent protein emits fluorescence of 507 nm. Oocytes with emitted fluorescence of 507 nm are classified into "light" and oocytes without emitted fluorescence is classified into "dark". FIG. 4 shows that these oocytes are stimulated with histamine and are classified by the presence or absence of response. As shown in FIG. 4, in the "light" oocytes, 85% of oocytes (34 out of 40 cells) respond to histamine. Namely, the histamine receptor gene can be injected in more than 85% of the oocytes. On the contrary, in the "dark" oocytes, 90% or more of oocytes can not respond to histamine (27 out of 28 cells). Namely, histamine receptor gene can not be injected in 90% or more of oocytes. Accordingly, it is demonstrated that frequency of injection of histamine receptor gene is high in the oocytes expressing green fluorescent protein.

As clearly demonstrated by the above fact, when the objective sample is co-injected with the fluorescent protein, the efficiency of injection of the objective sample can be calculated by existence of fluorescence as the indicator, as a result, sale or assignment of oocytes with guaranteed efficiency of sample injection is possible.

Next, a means for production, sale or assignment of oocytes obtained by the present invention for the specific use, which is exemplified by using oocytes injected with human histamine receptor cRNA, will be described.

However, gene for use of injection is not limited to cRNA, and DNA, RNA and oligonucleotide can be used.

The histamine receptor cRNA is injected into oocyte by using apparatus and method of the present invention. In this case, when a means for obtaining visual information such as a sensor for discriminating black and white color or CCD camera/digital camera is used, the oocytes to which cRNA is injected in the animal hemisphere, and the oocytes to which cRNA is injected in the vegetal hemisphere can be differentiated.

After gene injection, histamine receptor is expressed in the oocytes within 24 hours. After passing 24 hours from histamine receptor gene injection, membrane potential of the oocytes, in which histamine receptor may be expressed, is held at −60 mV by clamping with two electrodes. Under such conditions, the addition of a sample containing the histamine to the oocytes results in interacts between the histamines in the sample and the histamine receptors, and the signal transduction system in each oocyte is activated to generate an ionic current, then the electric response of the oocyte against histamine can be shown. The oocytes, after 24 hours, are stimulated with. 1 $\mu$M histamine and its electric current response is measured. FIG. 5 shows comparison of electric current response of the oocytes, to which a gene is injected in the animal hemisphere and in the vegetal hemisphere. As shown in FIG. 5, differences between electric current responses against histamine depending on the injected site of the gene are observed. Namely, the oocytes with good ligand response can be obtained in the case that gene is injected in the animal hemisphere rather than in the case that gene is injected in the vegetal hemisphere.

Consequently, for example, the oocytes group, to which histamine receptor cRNA is injected only in the animal hemisphere, can be used as good sensors with high sensitivity for histamine. Further, according to the present invention, sale or assignment of oocytes, to which the sample is injected into the specific position and depth, for the purpose of using them as sensors, can be made. As easily recognized by a person skilled in the art, examples of samples to be injected into oocytes according to the present invention to be used as sensors, include, but are not limited to, genes encoding receptors for any ligands other than for histamine, antibodies having reactivity for specific antigens, and glycoproteins having specific sugar chain limited.

Figure 6:
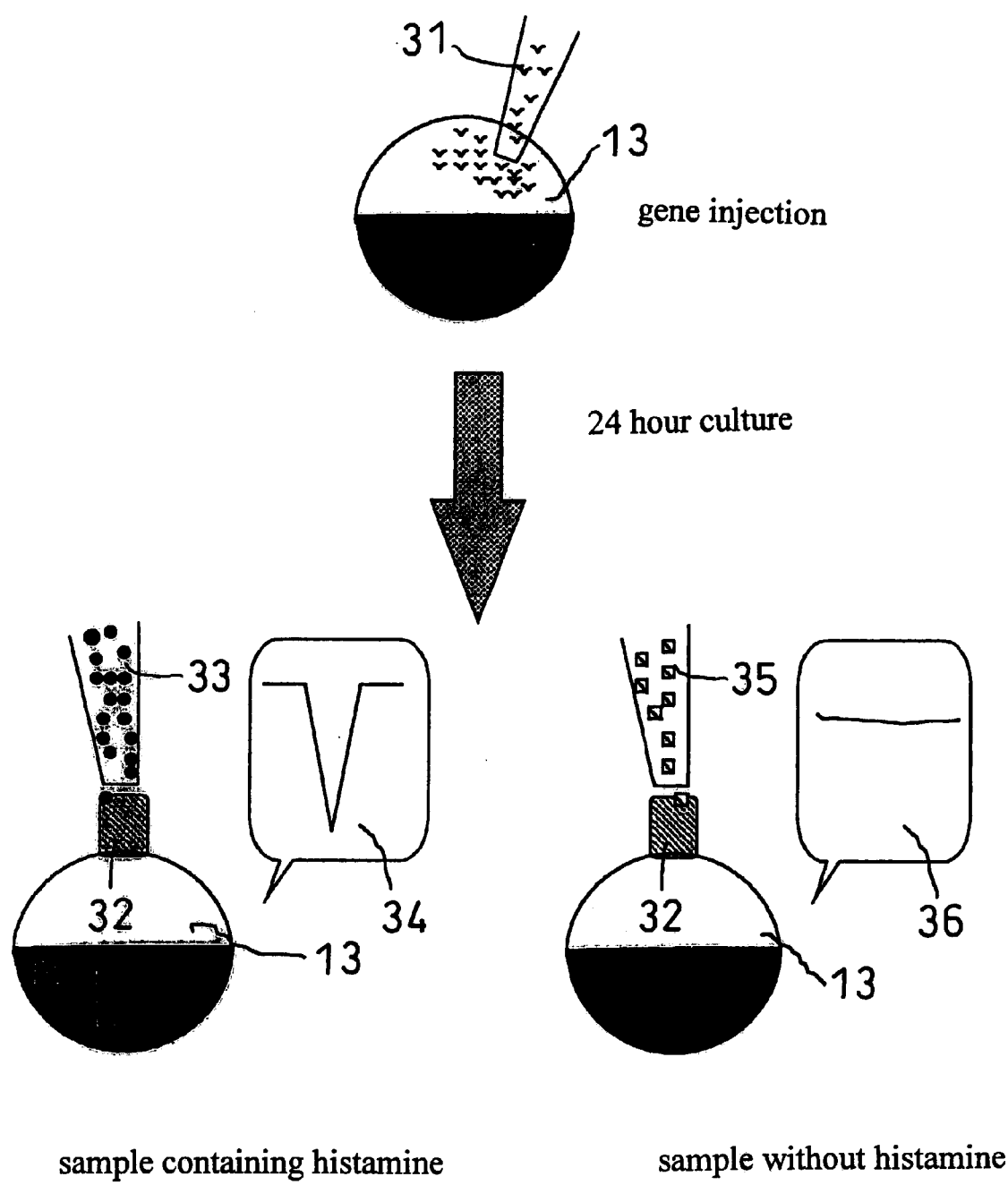
FIG. 6. Use of oocyte as a histamine sensor.

A histamine receptor gene 31 is injected into the oocyte 13 by using the apparatus assembled with the above constitution or using the above principles. In FIG. 6, the injection into the vegetal hemisphere is shown. After injection of the histamine receptor gene, histamine receptor 32 is expressed in the oocyte 13 within 24 hours. As discussed above, after passing 24 hours from the histamine receptor gene injection, the membrane potential of the oocytes, in which the histamine receptor 32 may be expressed, is held at −60 mV by clamping with two electrodes. Under such conditions, the addition of a sample 33 containing histamine to the oocyte 13 results in interaction between the histamines in the sample and the histamine receptors, and the signal transduction system in the oocyte is activated to generate an ionic current, then an electric response 34 of the oocyte 13 against histamine can be shown. In case that a sample 35 without histamine is added, since no substance, i.e., histamine, is available to anteract with the receptor, the oocyte 13 cannot respond to histamine 36.

The oocyte expressing histamine receptor response (against histamine containing samples) can be used as an indicator. Since mass production of oocytes having identical condition for injection of the sample is made possible by using the apparatus of the present invention, the amphibian oocytes can be used for screening ligand or antigen reacting with receptor and antibody respectively. The screening can be performed by using plurality of oocytes, in which a sample, such as gene, is injected under a substantially equal condition such that protein or other substances is expressed, and comparing the result of reactions of oocytes with defferent ligands.

Further, in the other use of the present invention, for example, the expressed protein can be extracted by crushing the oocytes in which protein is expressed. The protein and other products can be effectively extracted, for example, by controlling the condition for injection using apparatus of the present invention, and by using oocytes, to which a sample is injected into the animal hemisphere.

A method for transporting the oocytes according to the present invention, to each of which the sample is injected, will be described referring to FIG. 6. In case of sale and transport of the oocytes, the oocytes 13 are put into the vessel 21, to which the solution of buffer conventionally used for the amphibian oocytes dissolved with antibiotics, such as gentamicin sulfate, penicillin and streptomycin, is filled. The vessel 21 is packaged using a packaging material, such as styrene foam, and is preferably transported by maintaining a temperature at 4–25° C., more preferably at 18–22° C. by using a cold insulator 23 while avoiding shock, as shown in FIG. 3.

The composition of the solution is not limited, and the composition of the following can be used preferably. The solution PH is adjusted to 7.5.

| | |
|---|---|
| NaCl | 96 mM |
| KCl | 2 mM |
| $CaCl_2$ | 1.8 mM |
| $MgCl_2$ | 1 mM |
| HEPES | 5 mM |
| Gentamicin sulfate | 50 $\mu$g/ml |
| Sodium pyruvate | 2.5 mM |
| Penicillin | 10 U/ml |
| Streptomycin | 10 $\mu$g/ml |

The preferable vessels for sale and transport are not limited. Preferably, oocytes can move relatively freely inside the vessels with cap being freely opened and closed, and the solution is preferably filled to about 95% of the vessel volume. For example, in case of a conical tube of 50 ml, preferably about 100–200 oocytes, more preferably about 130–180 oocytes, are contained. This ratio corresponds to about 0.3–0.5 ml/oocyte, which can be varied depending on types of oocytes and types of vessels.

Figure 7:
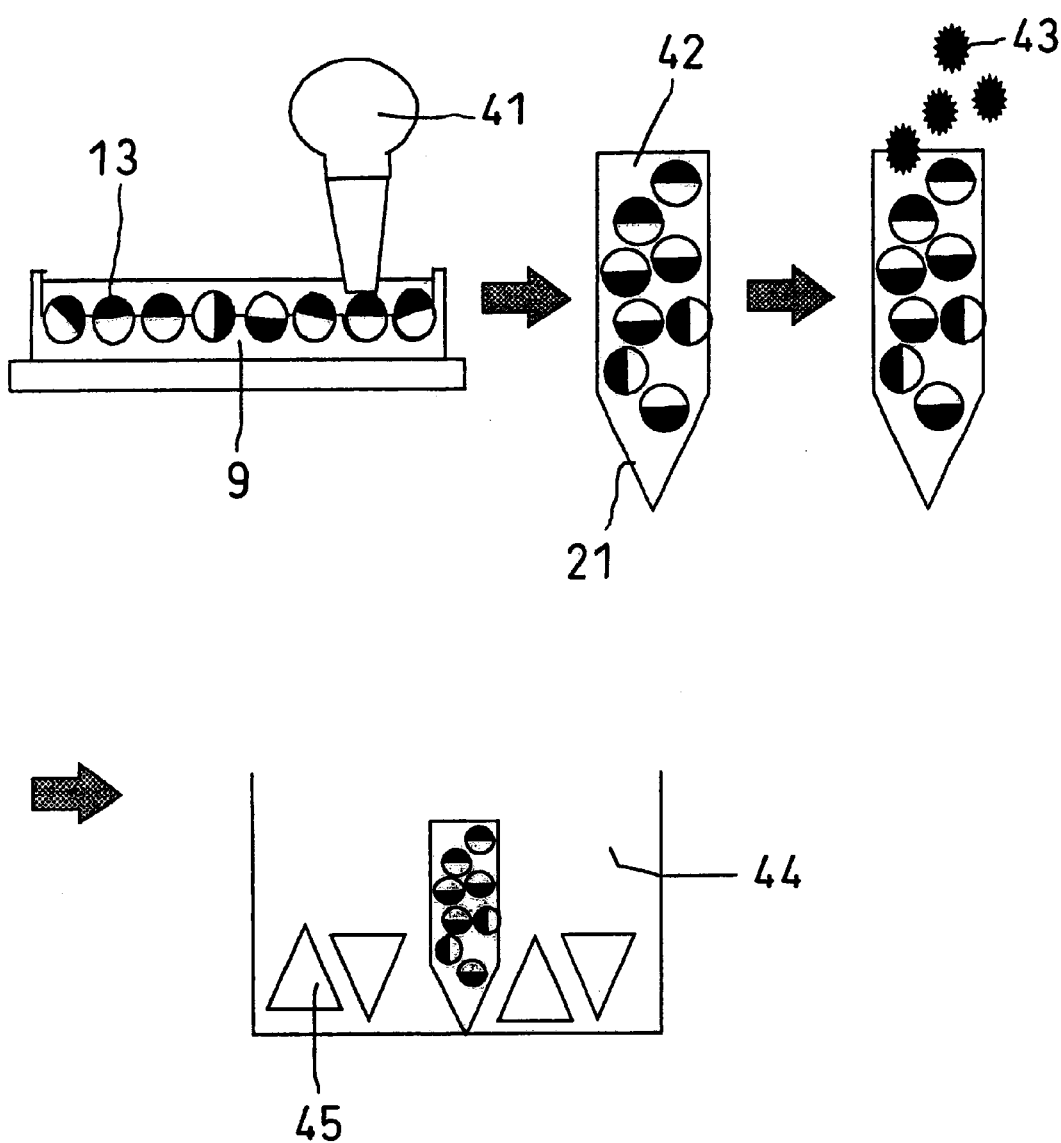
FIG. 7. A method of transferring oocytes after injection of sample.

As shown in FIG. 7, the oocyte 13, to which the sample has been injected, is recovered from the tray 9 by using a syringe 41. In this time, based on the recorded information, any one of the oocytes, to which the sample is injected into the animal hemisphere or the vegetal hemisphere, can be recovered. The recovered oocytes are transferred into the vessel 21. A buffer solution for Amphibia 42 is filled in the vessel 21, and the solution is exchanged for several times. After several exchanges, new buffer solution for Amphibia 42 is filled in the the vessel 21 again, and a preferable amount of antibiotics 43 is added thereto. The cover of the tube is closed and put into the outer case 44 with a cold insulator. The outer case 44 is filled with a packaging material 45 to fix the vessel 21 therein and transported to the customer by conventional transporting means.

By this method, the vessel can be transported to the customer without damaging the function of oocytes to which the sample is injected.

In the occasion of sale or assignment, the information including date of injection, place of injection of sample, condition for injection such as depth, recovery rate and term for guarantee of quality is provided. Ppaper describing such information may be attached or a label 22 may be attached to the vessel 21 containing the oocytes (FIG. 3).

If a gene is injected, about 24 hours is required for its expression, and the life-span of the oocytes is about 7 days after injection, preferably about 5 days for safety. Consequently, it is preferable to describe a date and time of injection and, a corresponding description indicating that "best use before X X (day-month)" in order to clearly indicate an effective term for use after injection.

As for the injection site of the oocyte, a sample can be injected to the animal hemisphere in about 80% of oocytes by using the above tray, and it is also possible to improve expression efficiency based on the accumulated information in the apparatus as well as using co-expression using the present apparatus.

EFFECT OF THE INVENTION

According to the present invention, the sample can be injected into the oocytes of Amphibia, such as frog, with a constant depth precisely such that mass production of such oocytes having an identical quality and the injection can be rapidly and efficiently performed. Quality of an oocyte or an area of needle injection can be recorded as the information.

Further, the oocytes obtained by the method of the present invention and into which the sample is injected in the specified position and depth, can be recovered, and the efficiency of injection of sample is guaranteed for the purpose of sale or assignment. In addition, selling or assigning of the oocytes can be made by specifying the use depending on the type of the injected sample.

What is claimed is:

1. An apparatus for microinjection of at least one sample into amphibian oocytes comprising:
   a tray with a plurality of wells each of which has an aperture with a maximum diameter longer than a diameter of the amphibian oocytes for holding a plurality of the amphibian oocytes while allowing the amphibian oocytes to rotate freely so as to take a stable orientation according to a respective center of gravity;
   at least one injection needle for injecting the sample into each of said amphibian oocytes;
   a driving means for moving said tray relative to said injection needle; and
   a controlling means for controlling said movement in response to a predetermined depth of said injection needle for said tray or said amphibian oocytes during the injection of the sample, and injecting the sample into a plurality of amphibian oocytes at said depth.

2. The apparatus according to claim 1, wherein the driving means is formed to drive the position of the tray relative to the injection needle in a three dimensional manner.

3. The apparatus according to claim 1, further comprising an information obtaining means for obtaining visual information on the amphibian oocytes during the injection of the samples.

4. The apparatus according to claim 3, wherein the obtaining means for the visual information of the amphibian oocytes is a camera.

5. The apparatus according to claim 3, further comprising a means for connecting the visual information of each of the amphibian oocytes collected by the information obtaining means with a position of a respective oocyte on the tray.

6. The apparatus according to claim 3, further comprising a memorizing means for memorizing the visual information.

7. The apparatus according to claim 1, wherein at least one of the wells has a cylindrical structure with a flat base or with a conical base having an angle of no less than 90 degree.

8. The apparatus according to claim 1, wherein at least one of the wells has a cylindrical structure with a flat base or with a conical base having a maximum diameter of 1.4–2 mm.

9. The apparatus according to claim 1, wherein at least one of the wells has a cylindrical structure with a flat base or with a conical base having a maximum diameter of 105–150% of a diameter of the amphibian oocytes.

10. The apparatus according to claim 1, wherein a position on a surface of the oocytes on the tray contacted by the injection needle is detected by at least one of visual information, a pressure change, a temperature change, an electrical change, a moisture change, and a pH change.

11. A system for microinjection of at least one sample into amphibian oocytes comprising:
    a tray with a plurality of wells each of which has an aperture with a maximum diameter longer than a diameter of the amphibian oocytes for holding a plurality of the amphibian oocytes while allowing the amphibian oocytes to rotate freely so as to take a stable orientation according to a respective center of gravity;
    at least one injection needle for injecting said sample into each of said amphibian oocytes;
    a driving means for moving a position of said tray relative to said injection needle,
    a controlling means for controlling said movement;
    an information obtaining means for obtaining visual information on said amphibian oocytes during the injection of said sample; and
    a memorizing means for accumulating said information, and injecting said sample into said amphibian oocytes.

12. The system according to claim 11, wherein at least one of the wells has a cylindrical structure with a flat base or with a conical base having a maximum diameter of 1.4–2 mm.

13. The system according to claim 11, wherein the well has a cylindrical structure with a flat base or with a conical base having a maximum diameter of 105–150% of a diameter of the amphibian oocytes.

14. A method for microinjection of at least one sample into amphibian oocytes, comprising the steps of:
    providing an apparatus having a tray with a plurality of wells of cylindrical structure with a flat base or with a conical base having a maximum diameter of 105–150% of a diameter of the amphibian oocytes for holding a plurality of the amphibian oocytes while allowing the amphibian oocytes to rotate freely so as to take a stable orientation according to a respective center of gravity, and at least one injection needle for injecting the sample into said amphibian oocytes;
    setting a depth of said injection needle for said tray or said amphibian oocytes as a first depth;
    injecting the sample into a first oocyte of said amphibian oocytes using said injection needle at said first depth;
    automatically moving said tray relative to said injection needle; and subsequently injecting the sample into a second oocyte of said amphibian oocytes by inserting said injection needle to said first depth.

15. A method for microinjection of at least one sample into amphibian oocytes, comprising the steps of:
providing an apparatus having a tray with a plurality of wells of cylindrical structure with a flat base or with a conical base having a maximum diameter of 105–150% of a diameter of the amphibian oocytes for holding a plurality of the amphibian oocytes while allowing the amphibian oocytes to rotate freely so as to take a stable orientation according to a respective center of gravity, and at least one injection needle for injecting the sample into said amphibian oocytes;
injecting the sample into a first oocyte of said amphibian oocytes using said injection needle;
moving said tray relative to said injection needle;
subsequently injecting the sample into at least a second oocyte of said amphibian oocytes using said injection needle;
obtaining a visual condition of oocyte during the injection of said sample as visual information; and
accumulating said visual information.

16. The method according to claim 14, wherein the said sample is a gene or protein.

17. The method according to claim 14, wherein the said sample contains a fluorescent substance.

18. The method according to claim 14, comprising a step of controlling an amount of sample injected in the said first oocyte and an amount of sample injected in the said second oocyte are set to substantially equal amounts.

19. An apparatus for microinjection of at least one sample into amphibian oocytes, comprising:
a tray with a plurality of apertures on each of which one of said amphibian oocytes is placed;
at least one injection needle for injecting the sample into each of said amphibian oocytes;
a driving means for moving said tray relative to said injection needle; and
a controlling means for controlling said movement in response to a predetermined depth of said injection needle for said tray or said amphibian oocytes to inject the sample,
wherein each of said apertures has a size allowing free rotation of each of said amphibian oocytes so as to take a stable orientation according to its center of gravity.

20. A system for microinjection of at least one sample into amphibian oocytes, comprising
a tray with a plurality of apertures on each of which one of said amphibian oocytes is placed;
at least one injection needle for injecting the sample into each of said amphibian oocytes;
a driving means for moving said tray relative to said injection needle;
a controlling means for controlling said movement;
an information obtaining means for obtaining visual information on said amphibian oocytes during the injection of the sample; and
a memorizing means for accumulating said visual information,
wherein each of said apertures has a size allowing free rotation of each of said amphibian oocytes so as to take a stable orientation according to its center of gravity.

21. A method for microinjection of at least one sample into amphibian oocytes, comprising the steps of:
providing an apparatus having a tray with a plurality of apertures on each of which one of said amphibian oocytes is placed, and at least one injection needle for injecting the sample into each of said amphibian oocytes, each of said apertures having a size allowing free rotation of each of said amphibian oocytes so as to take a stable orientation according to its center of gravity;
setting a depth of said injection needle for said tray or said amphibian oocytes as a first depth;
injecting the sample into an oocyte on a first aperture among said plurality of apertures using said injection needle to said first depth;
automatically moving said tray relative to said injection needle; and
subsequently injecting the sample into an occyte on at least a second aperture among said plurality of apertures using said injection needle to said first depth.

22. An apparatus for microinjection of at least one sample into amphibian oocytes, comprising:
a tray with a plurality of apertures each of which is placed with one of said amphibian oocytes;
at least one injection needle for injecting the sample into each of said amphibian oocytes;
a driving means for moving said tray relative to said injection needle so as to place said injection needle inside said tray and into at least one of said amphibian oocytes; and
a controlling means for controlling the movement of the driving means,
wherein each of said apertures has a size sufficient for each of said amphibian oocytes to freely rotate inside each of said apertures respectively so as to rotate to a stable orientation under gravity.

23. An apparatus for microinjection of at least one sample into amphibian oocytes, comprising:
a tray with a plurality of apertures each of which is placed with one of said amphibian oocytes;
at least one injection needle for injecting the sample into each of said amphibian oocytes;
a driving means for moving said tray relative to said injection needle so as to place said injection needle inside said tray and into at least one of said amphibian oocytes; and
a controlling means for controlling the movement of the driving means;
an information obtaining means for obtaining visual information on said amphibian oocytes while said injection needle is injecting said sample into said amphibian oocytes; and
a memorizing means for accumulating said visual information,
wherein each of said apertures has a size sufficient for each of said amphibian oocytes to freely rotate inside each of said apertures respectively so as to rotate to a stable orientation under gravity.

24. A method for microinjection of at least one sample into amphibian oocytes, comprising the steps of:
providing a tray with a plurality of apertures each of which is placed with one of said amphibian oocytes, and at least one injection needle for injecting the sample into each of said amphibian oocytes, each of said apertures having a size sufficient for said amphibian oocyte to freely rotate inside each of said apertures respectively so as to rotate to a stable orientation under gravity;

setting a depth for said injection needle to be inserted into each of said amphibian oocytes consistently;

automatically moving said tray to said injection needle so as to inject the sample into each of said amphibian oocytes sequentially; and injecting the sample into each of said amphibian oocytes at said depth.

25. The system according to claim 11, wherein at least one of the wells has a cylindrical structure with a flat base or with a conical base having an angle of no less than 90 degrees.

26. The method according to claim 14, wherein the conical base has an angle of no less than 90 degrees.

27. The method according to claim 15, wherein the conical base has an angle of no less than 90 degrees.

* * * * *